US00PP19440P2

(12) United States Plant Patent
Burton

(10) Patent No.: US PP19,440 P2
(45) Date of Patent: Nov. 11, 2008

(54) ***PHORMIUM* PLANT NAMED 'RUBY TUESDAY'**

(50) Latin Name: *Phormium cookianum*
Varietal Denomination: Ruby Tuesday

(76) Inventor: Stephen Burton, 1896 Hamilton Road, Cambridge (NZ)

( * ) Notice: Subject to any disclaimer, the term of this patent is extended or adjusted under 35 U.S.C. 154(b) by 0 days.

(21) Appl. No.: 11/895,729

(22) Filed: Aug. 27, 2007

(51) Int. Cl.
*A01H 5/00* (2006.01)

(52) U.S. Cl. ..... Plt./373; Plt./263.1
(58) Field of Classification Search ..... Plt./373, Plt./263.1, 226
See application file for complete search history.

*Primary Examiner*—Kent L. Bell
*Assistant Examiner*—June Hwu

(57) ABSTRACT

A new cultivar of *Phormium* plant named 'Ruby Tuesday' that is characterized by a semi-upright habit and red/burgundy leaves that retain their color as the plant ages.

1 Drawing Sheet

Botanical classification: *Phormium cookianum.*
Variety denomination: 'Ruby Tuesday'.

BACKGROUND OF THE INVENTION

The present invention relates to a new and distinct cultivar of *Phormium* plant botanically known as *Phormium cookianum* and hereinafter referred to by the cultivar name 'Ruby Tuesday'.

The new cultivar originated from seeds collected and grown from the female or seed parent plant *Phormium cookianum* 'Purpurea' (not patented). The male or pollen parent plant is unknown. 'Ruby Tuesday' was selected as a single plant by the inventor in a cultivated area of Cambridge, New Zealand in 2001.

Asexual reproduction by division of the new cultivar 'Ruby Tuesday' was first performed in 2001 in Cambridge, New Zealand. Since that time, under careful observation, the unique characteristics of the new cultivar have been uniform, stable and reproduced true to type in successive generations of asexual reproduction.

SUMMARY OF THE INVENTION

The following represent the distinguishing characteristics of the new *Phormium* cultivar 'Ruby Tuesday'.

1. *Phormium* 'Ruby Tuesday' exhibits a semi-upright habit.
2. *Phormium* 'Ruby Tuesday' exhibits red/burgundy leaves that retain their color as the plant ages.

The new cultivar 'Ruby Tuesday' is distinguishable from the female parent plant by the following characteristics:

1. 'Ruby Tuesday' has red/burgundy colored leaves. The leaves of 'Purpurea' are browner.
2. 'Ruby Tuesday' has a shorter overall height.

The closest comparison cultivars as *Phormium* 'Purple Haze' (not patented) and *Phormium* 'Dark Delight' (not patented).

The new cultivar 'Ruby Tuesday' is distinguishable from 'Purple Haze' by the following characteristics:

1. 'Ruby Tuesday' has a more erect habit.
2. 'Ruby Tuesday' has red/burgundy colored leaves. The leaves of 'Purple Haze' are grey-brown.

The new cultivar 'Ruby Tuesday' is distinguishable from 'Dark Delight' by the following characteristics:

1. 'Ruby Tuesday' has wider leaves.
2. 'Ruby Tuesday' has red/burgundy colored leaves. The leaves of 'Dark Delight' are more purple.

BRIEF DESCRIPTION OF THE DRAWING

The accompanying photograph illustrates the distinguishing traits of *Phormium* 'Ruby Tuesday'. The plant in the photograph shows an overall view of a 1 year old plant. The photograph was taken using conventional techniques and although colors may appear different from actual colors due to light reflectance it is as accurate as possible by conventional photographic techniques.

BOTANICAL DESCRIPTION OF THE PLANT

The following is a detailed description of the new *Phormium* cultivar named 'Ruby Tuesday'. Data was collected in Cambridge, New Zealand from 1 year old field grown plants. The time of year was Winter in the Southern Hemisphere and the temperature range was 0 to 20 degrees Centigrade during the day and −4 to 12 degrees Centigrade at night. No photoperiodic treatments or growth retardants were used. Color determinations are in accordance with The Royal Horticultural Society Colour Chart 2001 edition, except where general color terms of ordinary dictionary significance are used. The growing requirements are similar to the species. 'Ruby Tuesday' has not been tested under all possible conditions and phenotypic differences may be observed with variations in environmental, climatic, and cultural conditions, however, without any variance in genotype.

Botanical classification: *Phormium cookianum* 'Ruby Tuesday'.
Use: Ornamental perennial shrub.
Vigor: High.
Growth rate: Medium.
Growth habit: Compact with many pups.
Plant shape: Rounded, semi-erect.
Suitable container size: 3.3 L.
Height: Average 1.3 m in height.
Width: Average 1.0 m in width.

Low temperature tolerance: −5 Centigrade.
High temperature tolerance: 30 Centigrade.
Propagation: Division.
Crop time: 48 weeks to produce a finished plant from division.
Root system: Fine and fibrous.
Lateral Branches:
*Quantity.*—Approximately 10 to 15.
Foliage:
*Texture.*—Coriaceous.
*Leaf arrangement.*—Alternatively branched distichous fans.
*Compound or single.*—Single.
*Leaf shape.*—Lanceolate.
*Leaf apex.*—Acute.
*Leaf base.*—Attenuate.
*Leaf length.*—Average 1.3 m in length.
*Leaf width.*—Average 65 mm in width.
*Pubescence.*—Absent.
*Leaf margin.*—Entire.
*Young leaf color* (*upper surface*).—N77A.
*Young leaf color* (*lower surface*).—N187A.
*Mature leaf color* (*upper surface*).—N187A.
*Mature leaf color* (*lower surface*).—200A.
*Vein color* (*upper surface*).—1C.
*Vein color* (*lower surface*).—26A.
*Durability of foliage to stress.*—Moderate to high.
Flowers: Flowers have not been observed.
Disease and Insect Resistance: Plants of the new *Phormium* have not been observed for disease or insect resistance.

What is claimed is:

1. A new and distinct variety of *Phormium* plant named 'Ruby Tuesday' as described and illustrated.

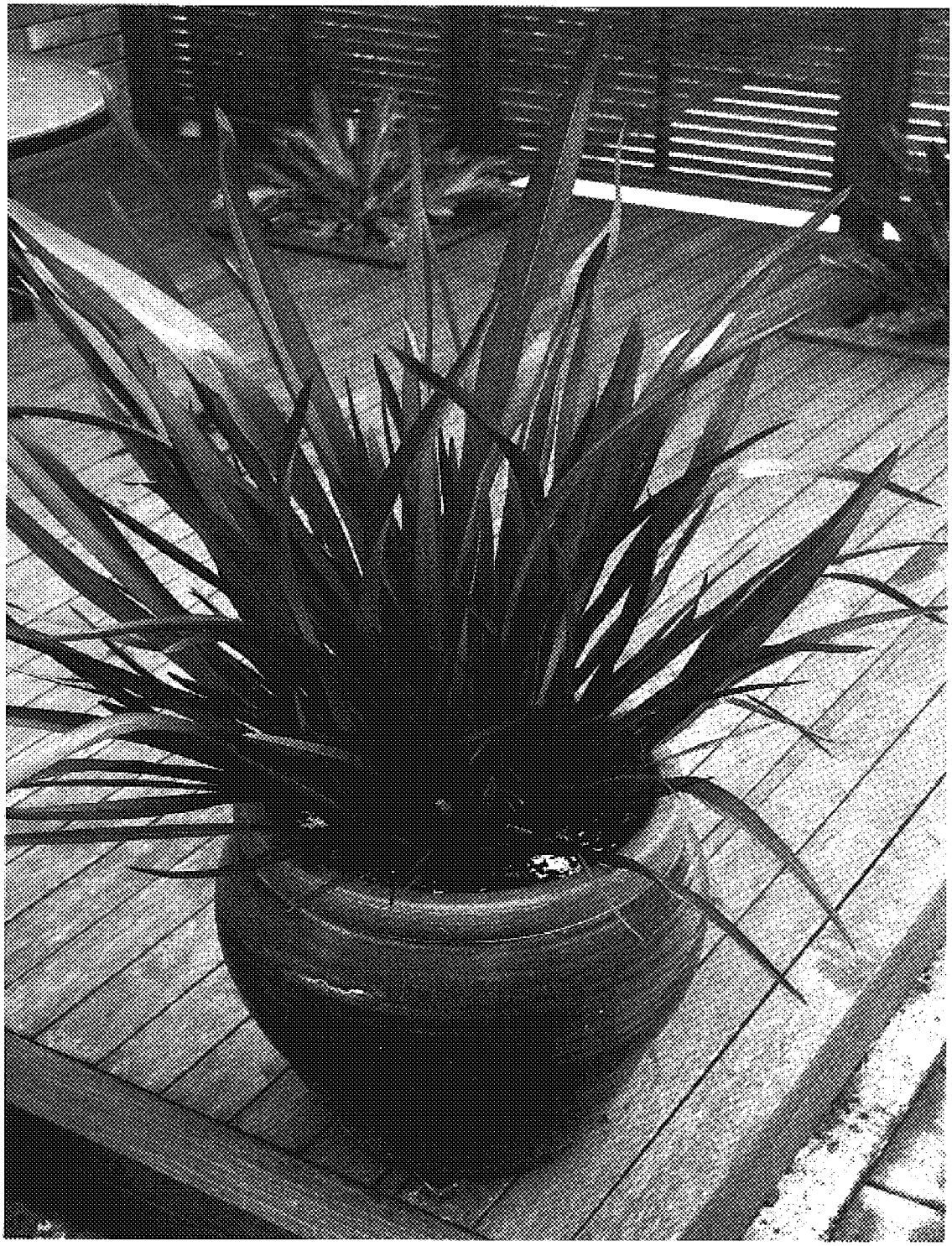

* * * * *